United States Patent

Moriya et al.

[11] Patent Number: 5,106,189
[45] Date of Patent: Apr. 21, 1992

[54] ZEEMAN ATOMIC ABSORPTION SPECTROPHOTOMETER

[75] Inventors: Kazuo Moriya, Katsuta; Susumu Taira, Ageo, both of Japan

[73] Assignee: Hitachi, Ltd., Tokyo, Japan

[21] Appl. No.: 669,513

[22] Filed: Mar. 14, 1991

[30] Foreign Application Priority Data

Mar. 16, 1990 [JP] Japan ............................. 2-66630

[51] Int. Cl.5 ...................... G01N 21/72; G01N 21/74
[52] U.S. Cl. ..................................... 356/307; 356/312; 356/315
[58] Field of Search ............... 356/307, 311, 312, 315, 356/316

[56] References Cited

U.S. PATENT DOCUMENTS 5,015,093 5/1991 Rogasch ............................. 356/307

FOREIGN PATENT DOCUMENTS 55-94144 7/1980 Japan.
58-5632 1/1983 Japan.

Primary Examiner—F. L. Evans
Attorney, Agent, or Firm—Antonelli, Terry, Stout & Kraus

[57] ABSTRACT

A Zeeman atomic spectrophotometer comprising a sample heating means for atomizing a sample, a means for applying a magnetic flux to the atomized sample and a ceramic film coated on at least tips of pole pieces which are disposed facing the heated sample. As the tips of the pole pieces are coated with a ceramic film, the measuring accuracy of the Zeeman atomic absorption spectrophotometer becomes high and stable over a very long term.

10 Claims, 3 Drawing Sheets

ZEEMAN ATOMIC ABSORPTION SPECTROPHOTOMETER

BACKGROUND OF THE INVENTION

The present invention relates to a Zeeman atomic absorption spectrophotometer for analyzing an inorganic element in a sample and more particularly to a Zeeman atomic absorption spectrophotometer having an improved magnet which applies a magnetic field to the sample in order to remove a background noise in detected signals.

In the conventional Zeeman atomic absorption spectrophotometer, the most popular one has a function which effectively corrects a background noise in an atomized sample by using a phenomenon that a light component polarized parallel to magnetic flux is absorbed by the atomized sample but a light component polarized perpendicular to the magnetic flux is scarcely absorbed by the atomized sample.

The Japanese Published Patent Laid-open No. 55-94144 (1980) and Japanese Patent Laid-open No. 58-5632 (1983) are cited as examples of such a device.

Such a conventional Zeeman atomic absorption spectrophotometer is superior with a measuring the sample in high accuracy, but recently a serious problem has been identified wherein a measuring error of the spectrophotometer increases over time.

SUMMARY OF THE INVENTION

The present invention has been accomplished to overcome the above mentioned problem of the conventional technique.

An object of the present invention is to provide a Zeeman atomic absorption spectrophotometer which is able to measure the sample with a high accuracy over a long time.

In order to solve this problem, the inventors of the present invention observed detected signals of the Zeeman atomic absorption spectrophotometer and found that the light component polarized parallel to magnetic flux which is absorbed by the atomized sample slightly decreases over a long time and the decreasing of the light component is based on the magnetic flux variation between pole pieces of the magnet which becomes weaker over a long time, and further the magnetic flux variation is caused by an absence of the tip portion of the pole piece which is heated to a very high temperature. The tip of the pole piece is generally made of iron and the inventors estimated that the tip of the pole piece is missing due to erosion because the pole piece is disposed in an atmosphere of a high temperature of about 3000° C., and a vaporized sample contains acid and is supplied between the pole pieces so as to approach the pole piece. Therefore, in the present invention, the tip portion of the pole piece is coated with a ceramic film to withstand the high temperature and acid.

DETAILED DESCRIPTION OF THE PREFERRED EMBODIMENTS

Figure 6:
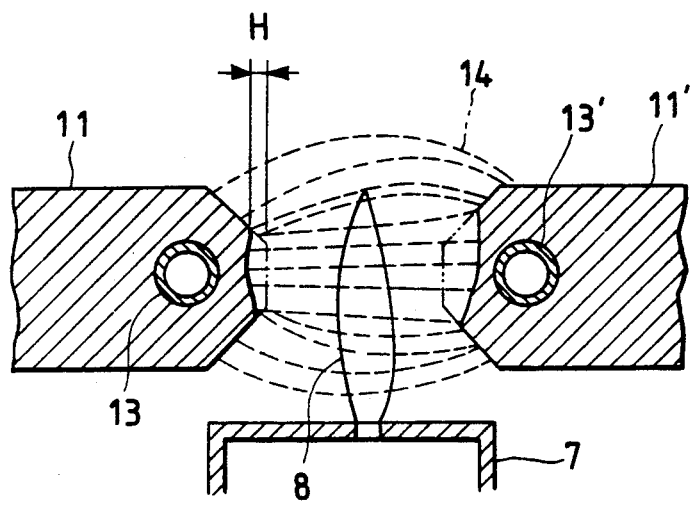
FIG. 6 is a cross-sectional view of the pole piece which shows the problem of the conventional Zeeman atomic absorption spectrophotometer.

FIG. 6 is a schematic cross-sectional view of the pole piece showing lines of magnetic force. In FIG. 6, numeral 7 denotes a burner head, 8 a flame, 11, 11' pole pieces, 13, 13' pipes for conducting refrigerant such as water and 14 lines of magnetic force in the magnetic flux.

In an experiment performed by the inventors of the present invention, a decrease in the magnetic flux density which is measured by analyzing the signal strength of the polarized light component was 20 to 30% together with disordered and non-uniform lines of magnetic force, and a decrease in the sensitivity of the atomic absorption was 10 to 30%. The magnet usually provided a magnetic flux density 8 to 11 K gauss in the central portion of the two pole pieces 11, 11'; and it is estimated that the magnetic flux density decreases to 10 K gauss when the tip of the pole piece 11, 11' is eroded more than 3 mm.

If the decrease of the magnetic flux density is 10% when analyzing Zinc (Zn) or Mercury (Hg), it is found that the sensitivity of the atomic absorption decreases 10 to 30% and the normal Zeeman effect can not be expected such that normal operation of the Zeeman atomic absorption spectrophotometer is not achieved.

Generally, the Zeeman atomic absorption spectrophotometer is able to measure various kinds of samples, and many samples contain acid. Furthermore, the temperature of the flame 8 becomes 3000° C. when using a high temperature burner which supplies a mixture with nitrogen suboxide and acetylene gas. Therefore it is easily estimated that the pole piece will be significantly eroded.

In the present invention, the tip of the pole piece is coated with a ceramic film which is able to withstand the high temperature and acid and further does not have an undesirable effect on the magnetic characteristics of the pole piece.

Figure 1:
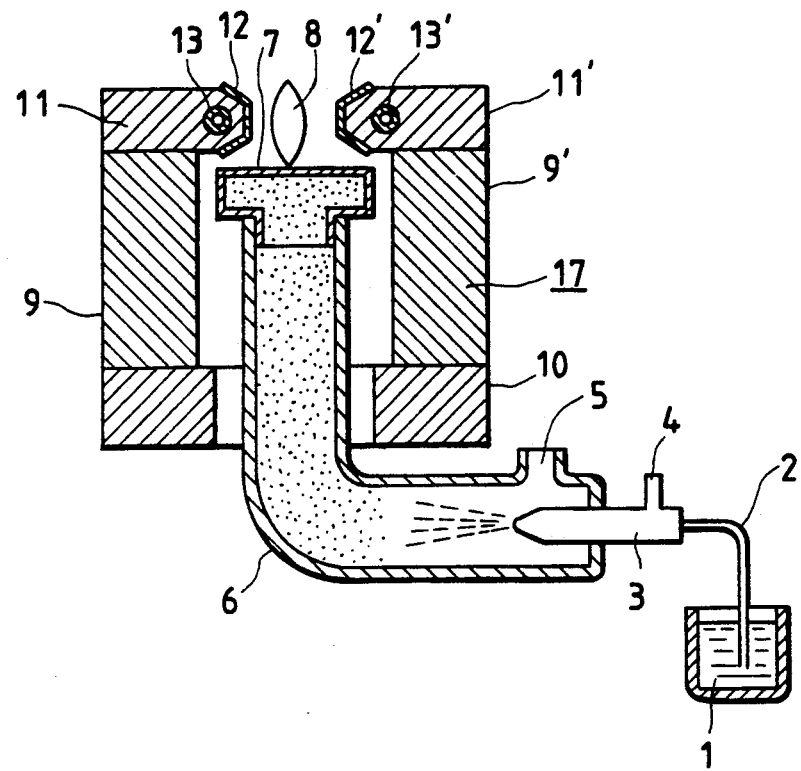
FIG. 1 is a diagrammatic cross-sectional view showing an embodiment of a Zeeman atomic absorption spectrophotometer in the present invention.

In FIG. 1, numeral 1 denotes a sample liquid, 2 a capillary tube, 3 a nebulizer, 4 an air inlet, 5 a fuel gas inlet, 6 a burner chamber, 7 a burner head, 8 a flame, 9, 9' magnets, 10 a yoke, 11, 11' pole pieces, 12, 12' ceramic films coated on top of the pole pieces 11, 11', 13, 13' pipes for conducting refrigerant and 17 a magnet device consisting of magnets 9, 9', yoke 10 and pole pieces 11, 11'.

The sample liquid 1 is object of analysis which is supplied through the capillary tube 2 to the nebulizer 3 and is vaporized with compressed air supplied from the air inlet 4 connected to the nebulizer 3 based on the principle of a sprayer. The vaporized sample liquid from the nebulizer 3 is mixed with acetylene gas supplied from the fuel gas inlet 5, passes through the burner chamber 6, is emitted from the burner head 7, and is ignited so as to form the flame 8 on the burner head 7.

By the way, the flame 8 is disposed between the pole pieces 11, 11 of the magnet device 17, and magnetic flux density in the central position between the respective tips of the pole pieces 11, 11', that is, in the central position of the flame 8, is controlled so as to be about 8 to 11 K gauss. Pipes 13, 13' provided in the pole pieces 11, 11' supply cooling water as a refrigerant so as to cool the pole pieces 11, 11' and so as not to decrease the magnetic flux density generated by the pole pieces 11, 11' because the temperature of the flame 8 is about 2000° to 3000° C.

Figure 2:
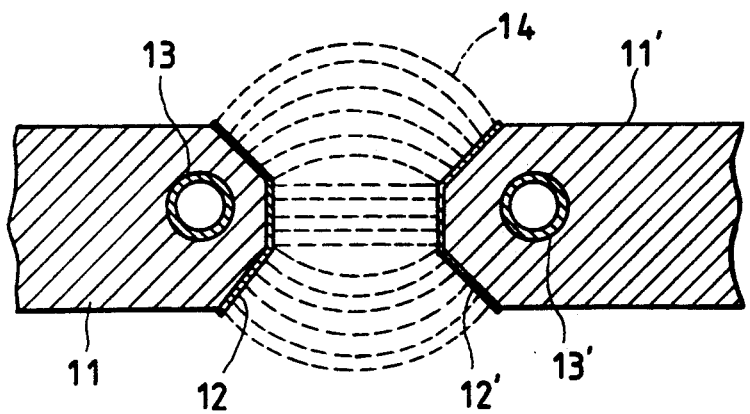
FIG. 2 is a cross-sectional view showing an embodiment of a pole piece of the Zeeman atomic absorption spectrophotometer shown in FIG. 1.

An embodiment of the pole pieces 11, 11' in the present invention is shown in FIG. 2. The missing portions of the pole pieces 11, 11' which result in the decrease of the magnet flux density are estimated to be the tip portions of the pole pieces 11, 11' exposed to the atomized sample which contains acid and is at a very high temperature. Therefore, the tip portions of the pole pieces 11, 11' which face the flame 8 are coated with ceramic films 12, 12'. It is not always necessary to coat other portions except the tip or end portions of the pole pieces 11, 11'. Therefore, if the other portions except the tip or end portions of the pole pieces 11, 11' are eroded, there is no bad undesirable effect on the magnetic flux density which influences the Zeeman effect. Of course, the other portions of the pole pieces 11, 11' may be coated with ceramic films in order to prevent the erosion of the other portions. The technical feature of the present invention is in coating with a ceramic film at least the tip portion of the magnet which faces the flame 8 in order to prevent the decreasing of the flux density which has an undesirable influence on the Zeeman effect.

As stated above, as the tip portions of the pole pieces 11, 11' are coated with ceramic films, the life of the Zeeman atomic absorption spectrophotometer which has a high accuracy is remarkably extended.

Figure 3:
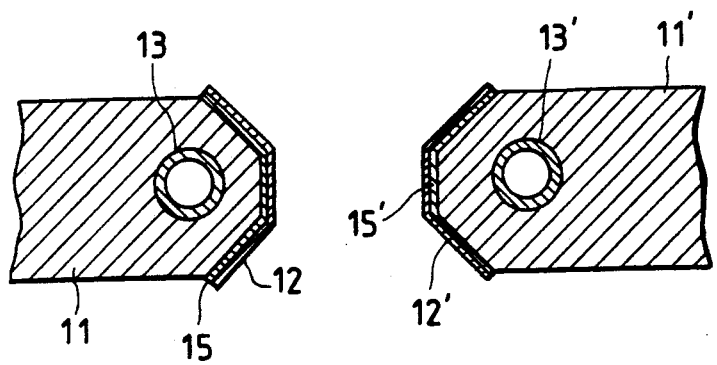
FIG. 3 is a cross-sectional view showing another embodiment of a pole piece of the Zeeman atomic absorption spectrophotometer shown in FIG. 1.

Another embodiment of the pole pieces 11, 11' in the present invention is shown in FIG. 3.

The pole pieces, 11, 11' are cooled by water, but are frequently heated to a fairly high temperature. The ceramic films 12, 12' which are directly coated on the pole pieces 11, 11' as shown in FIG. 2 tend to separate from the pole pieces. Therefore, in the embodiment shown in FIG. 3, the pole pieces 11, 11' are respectively coated with metal films 15, 15' such as nickel (Ni) or chromium (Cr) first and are further coated with ceramic films 12, 12' respectively on the metal films 15, 15' so as to form a double coating film consisting of the metal film and the ceramic film. Especially when using a double coating film consisting of a nickel film and the ceramic film, a heat-resistance temperature thereof becomes high and a corrosion resistance thereof becomes excellent.

Figure 4:
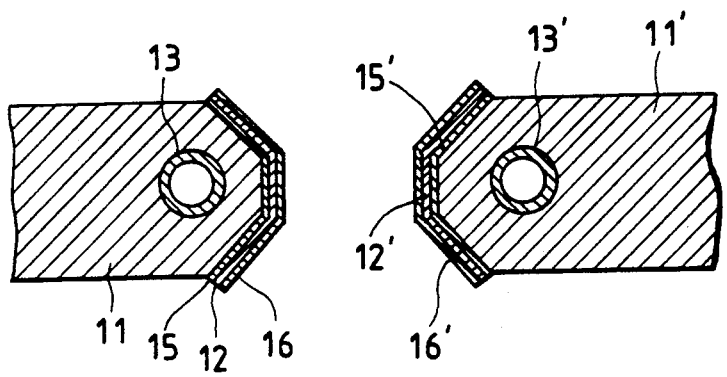
FIG. 4 is a cross-sectional view showing another embodiment of a pole piece of the Zeeman atomic absorption spectrophotometer shown in FIG. 1.

Further, FIG. 4 shows another embodiment of the pole pieces 11, 11' having a triple coating of films in the present invention.

For forming a ceramic coating film, there are various methods such as a vacuum deposition method, an ion plating method, a sputtering method, a plasma injection method, etc. However, it is difficult to coat a film having a high density with these methods which do not have any pin holes on the surface of the film. When the ceramics coating film is formed on the pole pieces by one of these methods, the film has many pin holes on the surface which allow some a corrosive substance such as acid, etc., to come in contact with the pole pieces through the pin holes of the film so as to cause the film to separate from the pole pieces. Accordingly, it becomes necessary to coat the ceramic film with a film of inorganic material such as glass so as to prevent the pole pieces from coming in contact with the corrosive substance through the pin holes. In FIG. 4, the tips of the pole pieces 11, 11' are coated with the metal films 15, 15' at first and are coated with the ceramic films 12, 12' on the metal films next, and are coated with the inorganic films 16, 16' on the ceramic films finally.

Figure 5:
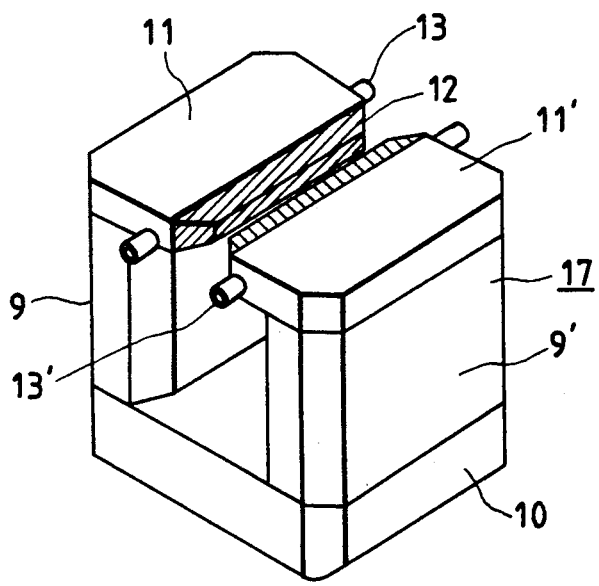
FIG. 5 is a perspective showing a magnet having the pole piece of the Zeeman atomic absorption spectrophotometer shown in FIG. 1.

FIG. 5 shows a perspective view of the magnet of the Zeeman atomic absorption spectrophotometer. The films are provided on tip portions of the pole piece shown with oblique lines in order to attain the object of the present invention.

Figure 7:
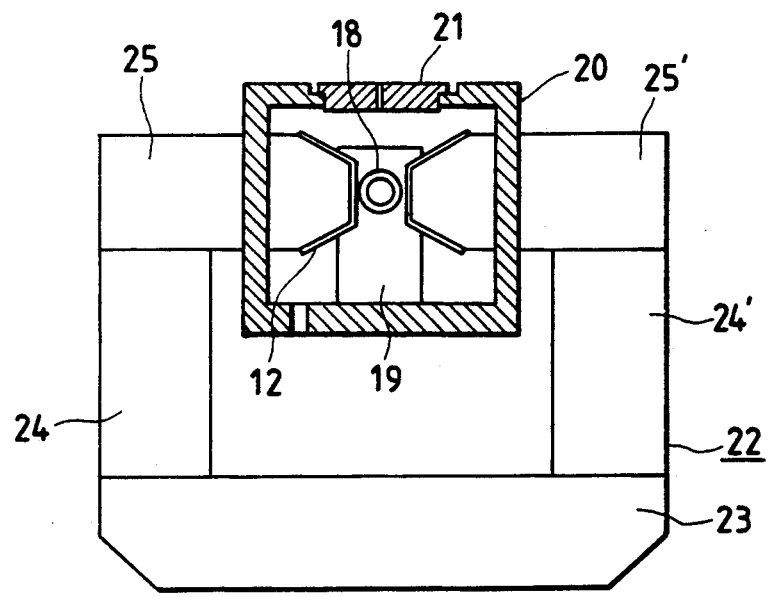
FIG. 7 is a cross-sectional view showing another embodiment which is applied to another tip of the Zeeman atomic absorption spectrophotometer.

FIG. 7 is another embodiment which is applied to a Zeeman atomic absorption spectrophotometer of the flameless type.

A liquid or solid sample is place in a cuvette 18 made of carbon which is heated by flowing an electric current of 200 to 500 amperes in the cuvette form an electrode 19 disposed on the end portions of the cuvette 18 so as to atomize the sample in the cuvette 18. The cuvette 18 is disposed between pole pieces 25, 25' of a magnet device 22 so as to produce the Zeeman effect. The magnet device 22 consists of a yoke 23, magnets 24, 24' and pole pieces 25, 25'. The pole pieces 25, 25' in the flameless type Zeeman atomic absorption spectrophotometer may be coated the same as the cases shown in FIGS. 2, 3, 4 in order to attain the object of the present invention.

As stated above, as the tips of the pole piece of the present invention are coated with ceramic films, the measuring accuracy of the Zeeman atomic absorption spectrophotometer becomes high and stable over a very long term.

We claim:

1. A Zeeman atomic spectrophotometer comprising:
   heating means for heating a sample to atomize the sample; and
   magnet means for applying a magnetic flux to the heated atomized sample, the magnet means including:
   a pole piece having a tip facing the heated atomized sample;
   a magnet magnetically connected to the pole piece; and
   a ceramic film provided on at least the tip of the pole piece.

2. A Zeeman atomic spectrophotometer as defined in claim 1, wherein the magnet means further includes a metal film provided on at least the tip of the pole piece, the ceramic film being provided on the metal film.

3. A Zeeman atomic spectrophotometer as defined in claim 2, wherein said metal film is made of nickel.

4. A Zeeman atomic spectrophotometer as defined in claim 1, wherein the magnet means further includes an inorganic film provided on the ceramic film.

5. A Zeeman atomic spectrophotometer as defined in claim 4, wherein said inorganic film is made of glass.

6. A Zeeman atomic spectrophotometer as defined in claim 1, wherein said heating means is a burner which burns a mixture of the sample and a fuel gas.

7. A Zeeman atomic spectrophotometer as defined in claim 1, wherein said heating means includes a cuvette in which the sample is disposed, and means for causing an electric current to flow through the cuvette to heat the cuvette and the sample disposed therein.

8. A Zeeman atomic spectrophotometer comprising:
heating means for heating a sample to atomize the sample; and
magnet means for applying a magnetic flux to the heated atomized sample, the magnet means including:
a pole piece having a tip facing the heated atomized sample;
a magnet magnetically connected to the pole piece;
a metal film provided on at least the tip of the pole piece;
a ceramic film provided on the metal film; and
an inorganic film provided on the ceramic film.

9. A Zeeman atomic spectrophotometer as defined in claim 8, wherein said heating means is a burner which burns a mixture of the sample and a fuel gas.

10. A Zeeman atomic spectrophotometer as defined in claim 8, wherein said heating means includes a cuvette in which the sample is disposed, and means for causing an electric current to flow through the cuvette to heat the cuvette and the sample disposed therein.

* * * * *